United States Patent [19]

Palepu et al.

[11] Patent Number: 5,336,669
[45] Date of Patent: Aug. 9, 1994

[54] CYCLOPHOSPHAMIDE MONOHYDRATE AND LACTOSE

[75] Inventors: Nageswara R. Palepu, Lansdale; Tomaz R. Herzyk, King of Prussia, both of Pa.

[73] Assignee: Erbamont, Inc., Dublin, Ohio

[21] Appl. No.: 65,076

[22] Filed: May 20, 1993

Related U.S. Application Data

[63] Continuation of Ser. No. 805,181, Dec. 10, 1991, abandoned.

[51] Int. Cl.$^5$ .................. A61K 31/715; A61K 31/66; A61K 47/00
[52] U.S. Cl. ...................... 514/53; 514/110; 514/960; 514/777
[58] Field of Search .................. 514/53, 110, 960, 777

[56] References Cited

U.S. PATENT DOCUMENTS

| | | | |
|---|---|---|---|
| 4,537,883 | 8/1985 | Alexander | 514/110 |
| 4,659,699 | 4/1987 | Francis | 514/53 |
| 5,036,060 | 7/1991 | Alam | 514/110 |

OTHER PUBLICATIONS

Kovalcik et al "The Stability of Cyclophosphamide . . ." Chem Abstract 108(4): 210088; 1988.

Primary Examiner—Gregory Hook
Attorney, Agent, or Firm—Thompson, Hine and Flory

[57] ABSTRACT

A parmaceutical preparation consisting essentially of a lyophilized cake of cyclophosphamide monohydrate and lactose prepared by the process of freezing cyclophosphamide, lactose and water, lyophilizing part of the water, obtaining and melting a supersaturated cyclophosphamide-lactose solution, precipitating cyclophosphamide as a hydrated polymorph, refreezing the solution and lyophilizing the water not bound to cyclophosphamide or lactose.

4 Claims, 2 Drawing Sheets

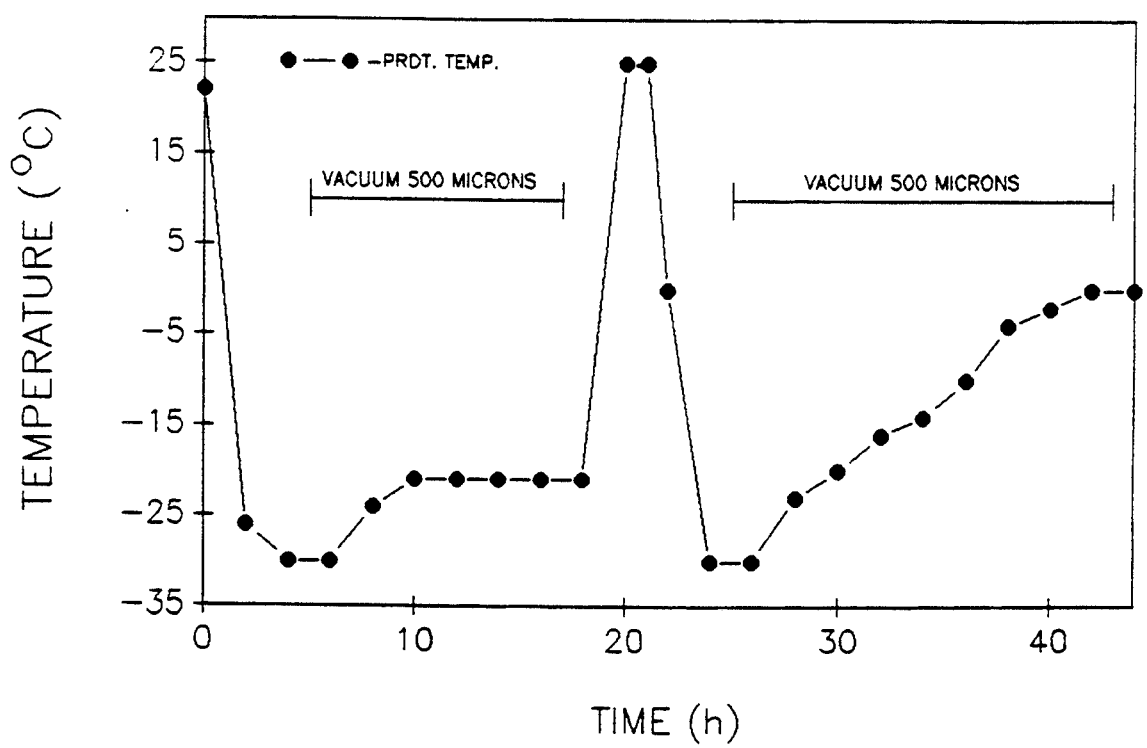

CYCLOPHOSPHAMIDE MONOHYDRATE AND LACTOSE

This is a continuation of co-pending application Ser. No. 07/805,181, filed Dec. 10, 1991, now abandoned.

BACKGROUND OF THE INVENTION

The present invention relates to the lyophilization of cyclophosphamide.

U.S. Pat. No. 4,537,883 to Alexander et al. (Mead Johnson & Co.) discloses various lyophilizates of cyclophosphamide. These lyophilizates are prepared by lyophilizing a solution of cyclophosphamide and one or more excipients and re-hydrating the product such that it contains about 4% moisture. The patent is based upon a comparative study of lyophilizate cakes and the dissolution time for lyophilizates of cyclophosphamide prepared using a number of excipients. The study concludes that the lyophilizate prepared with mannitol gives a better cake and faster dissolution time than the lyophilizates prepared with other excipients. The patent also teaches that the lyophilized cyclophosphamide-mannitol composition exhibits better thermal stability if it contains an equimolar amount of water based on cyclophosphamide. The preferred lyophilizate contains 20 parts cyclophosphamide, 1.25 to 2 parts water and 10 to 85 parts mannitol. Among the excipients evaluated in the patent are mannitol, sodium bicarbonate, lactose, polyvinyl pyrrolidone (PVP), arginine, and tartaric acid.

In lyophilizing cyclophosphamide, it is known that cyclophosphamide monohydrate is more stable than anhydrous cyclophosphamide. As a result, a practice has developed wherein in preparing lyophilized pharmaceutical preparations containing cyclophosphamide, the bound water or water of crystallization is removed from the cyclophosphamide in the lyophilizer and a small amount of water is back added to the composition to convert the less stable anhydrous cyclophosphamide product to the more stable monohydrate. This practice is described in U.S. Pat. No. 4,537,883 to Alexander and in T.R. Kovalcik and J.K. Guillory "The Stability of Cyclophosphamide in Lyophilized Cakes," J. Paren. Sci. & Tech., 42, No. 1, p. 29–37 (1988). It is also described in commonly assigned U.S. applications 07/597,965 and 07/583,896.

The process of back adding water is not satisfactory when using certain bulking agents, such as lactose, which take up the water which is back added to the composition. Such bulking agents compete with the cyclophosphamide for the water. Because these bulking agents have a higher affinity for water than cyclophosphamide, the cyclophosphamide may never be converted to the monohydrate as desired.

Published European Application 0 401 894 to Pharmachemie discloses a lyophilization process for preparing freeze-dried cyclophosphamide monohydrate without any bulking agent. Cyclophosphamide monohydrate is commercially available neat, i.e., without any bulking agent. This compound might be administered to patients directly but it is difficult to dissolve and hence difficult to reconstitute. Accordingly, it would be desirable to have a more readily dissolvable form of cyclophosphamide monohydrate. While not desiring to be bound, it is believed that lyophilizates in accordance with the invention described below may have a unique crystalline structure which renders them more easy to dissolve and reconstitute.

SUMMARY OF THE INVENTION

The present invention relates to a method for lyophilizing cyclophosphamide which overcomes the need to add water back to the lyophilizate to stabilize it and enables one to prepare lyophilizates of cyclophosphamide monohydrate using bulking agents such as lactose which have a strong affinity for water.

The method of the present invention comprises the sequential steps of:

freezing a bulk solution containing cyclophosphamide, a bulking agent, and water;

removing a portion of the water from said frozen solution by lyophilization, said water being removed in an amount such that upon melting said solution, a solution supersaturated with said cyclophosphamide frozen solution is formed;

melting said solution to produce a solution supersaturated with said cyclophosphamide and said bulking agent;

precipitating said cyclophosphamide as a hydrated polymorph;

refreezing said solution containing said precipitated cyclophosphamide; and removing by lyophilization the free water in said refrozen solution without removing water bound to said cyclophosphamide or said bulking agent to yield a lyophilizate of cyclophosphamide monohydrate.

The present invention further provides a pharmaceutical preparation comprising a lyophilized cake containing cyclophosphamide monohydrate and lactose. Previously, it was not believed to be possible to prepare lyophilizates of cyclophosphamide monohydrate and lactose because it was believed that water should be added back to the composition to form the monohydrate. Using this process, the lactose preferentially binds to the water added back to the composition and a lyophilizate of the less stable anhydrous cyclophosphamide is obtained.

BRIEF DESCRIPTION OF THE FIGURE

FIG. 2 is a pressure and product temperature diagram for the lyophilization cycle used in the Example.

DEFINITIONS

Figure 1:
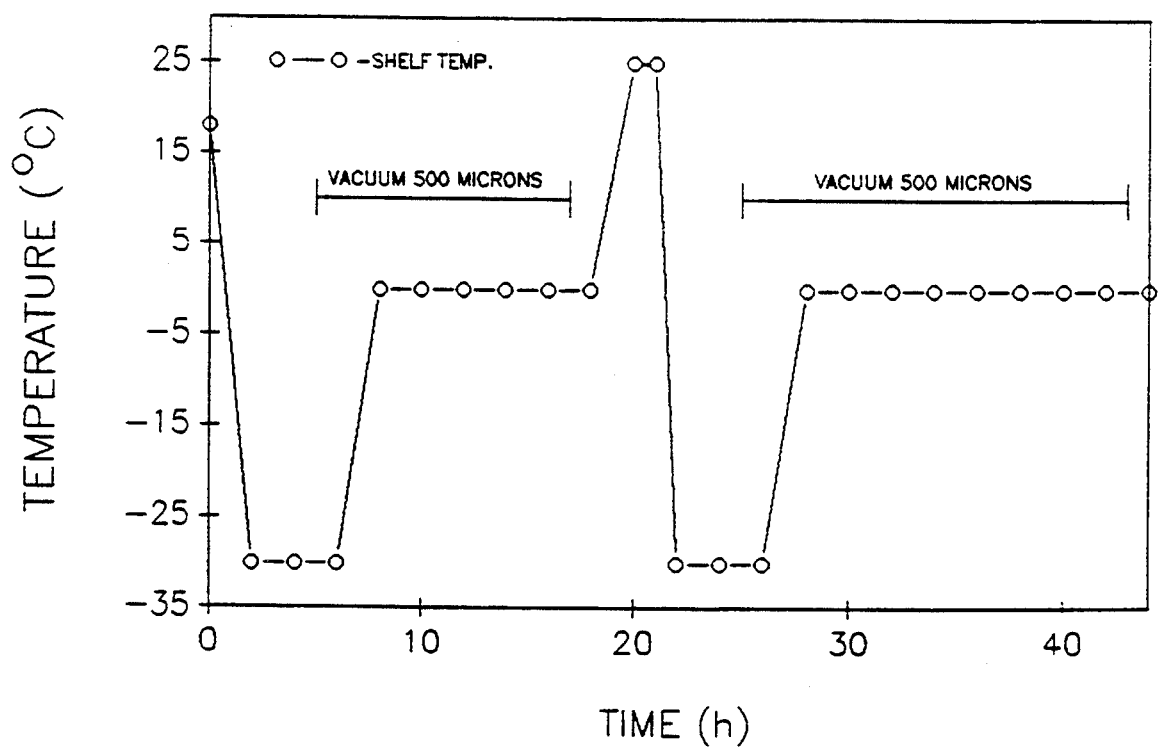
FIG. 1 is a pressure and shelf temperature diagram for the lyophilization cycle used in the Example.

The term "nominal volume" or "nominal vial volume" as used herein means the vial volume as stated by the manufacturer exclusive of headspace, i.e., not the total actual volume of the vial.

DETAILED DESCRIPTION

In accordance with the invention, a cyclophosphamide bulk solution is lyophilized in two stages to provide efficiently a storage stable composition without requiring further hydration to yield a stable lyophilized composition. In performing the lyophilization, the lyophilization conditions are controlled so that the cyclophosphamide is precipitated as a hydrated polymorph and then the process is completed under conditions which are carefully selected so that water bound to the cyclophosphamide as the monohydrate is not removed during the remainder of the lyophilization process. As initially precipitated, cyclophosphamide may have one or more molecules of water bound to it. For this reason, it is referred to as a "hydrated polymorph." The first molecule of water bound to the cyclophosphamide is believed to be more strongly bound to the compound and more energy is required to remove this molecule of water than is required to remove other water molecules subsequently bound to the compound.

The lyophilization process can be considered as occurring in two stages. In the first stage, a supersaturated solution of cyclophosphamide is produced from which hydrated cyclophosphamide polymorph is precipitated. In the second stage, any remaining unbound or free water any water not bound to the cyclophosphamide as the monohydrate is removed. The second stage procedure is more delicate than the first because water must be removed without removing the water bound to the cyclophosphamide as the monohydrate.

The first stage lyophilization may be carried out under harsher conditions than the second stage, e.g., at higher temperatures and/or lower pressures to sublimate a major portion of water from the frozen solution to produce a supersaturated solution of cyclophosphamide upon melting. In the second stage, care is taken not to generate the anhydrous cyclophosphamide by removing the water bound to the cyclophosphamide as the monohydrate. For this reason, the second stage may require milder conditions.

In the first stage lyophilization the vials are cooled to an initial temperature of $-15°$ C. or less and more preferably $-30°$ C. or less. The vials are held at the temperature about 4 to 5 hours. When the solution is completely frozen, the pressure is reduced and the condensor is activated. Pressures less than 8000 micron, preferably less than 750 microns and most preferably about 500 microns are used. The vials are held under this condition about one hour. The shelf temperature is then raised to about $0°$ C. and the vials gradually warm. As the vials warm, about 60 to 70% of the water is removed by the lyophilizer. This usually requires about 10 hours. Throughout this disclosure, times for various stages of lyophilization are sated. These times will vary depending upon a number of factors including the capacity and operation of the lyophilizer, the number of vials, the dosage, fill level, the nature of the bulking agent, etc.

The preferred bulking agent is lactose, but mannitol, lower molecular weight amino acids such as glycine, valine, etc. and other bulking agents described in U.S. Pat. No. 4,537,883 are also believed to be useful. Amorphous bulking agents such as bicarbonate and sorbitol are not believed to be useful in the process.

The bulk solution may contain about 2.5 to about 3.5% and preferably about 3.0 to 3.3% cyclophosphamide, and about 1 to 10% bulking agent. Amounts will vary with the selection of the bulking agent. For lactose, the bulk solution preferably contains about 3.0 to 3.3% (30–33 mg/ml) and most preferably 3% cyclophosphamide and 2 to 7% lactose (20–70 mg/ml). Cyclophosphamide-lactose cakes produced in accordance with the present invention most preferably contain about equal amounts of cyclophosphamide and lactose. While the amounts of lactose and cyclophosphamide disclosed above may be used, the ratio of lactose to cyclophosphamide generally ranges from about 0.3 to 1.7 parts lactose per 1 part cyclophosphamide.

The bulk solution is easily prepared by dissolving the bulking agent and cyclophosphamide in distilled or deionized water at room temperature. The cyclophosphamide can be obtained from Farmos Company as the crystalline monohydrate. The amorphous anhydrous cyclophosphamide could also be used to prepare the bulk solution.

The method of the present invention is generally practiced using 10 to 100ml vials (nominal volume). The bulk solution is added to provide 100 to 2000mg cyclophosphamide dosages as shown on the next table:

| Dosage | Nominal Vial Volume | Bulk Solution* |
|---|---|---|
| 100 mg | 10 cc | 3.3 ml |
| 200 mg | 20 cc | 6.6 ml |
| 500 mg | 30 cc | 17 ml |
| 1 g | 100 cc | 34 ml |
| 2 g | 100 cc | 68 ml |

*30 mg/ml cyclophosphamide

The first stage lyophilization is stopped when a majority and preferably about 60% to 70% of the water is removed. Enough water must remain in the vial after the first stage lyophilization to supply the water bound to the cyclophosphamide and the bulking agent and to dissolve the cyclophosphamide. In general, the amount of water in the vial should not be reduced to less than about 30% of the total contents of the vial. If more water than this is removed, incomplete conversion of the cyclophosphamide to the stable monohydrate may result.

The objective of the first stage lyophilization is to produce a supersaturated solution from which the cyclophosphamide precipitates as a hydrated polymorph on warming. When the desired amount of water has been removed, the vacuum and condensor are deactivated and the lyophilization chamber is allowed to warm to a temperature at which the solution melts and the cyclophosphamide precipitates from solution as a hydrated polymorph. This temperature is typically about $25°$ C. Any temperature which melts the cake can be used. The term "precipitate" is used herein because it is not entirely clear whether the hydrated polymorph is crystalline or not and hence it is not clear whether the term "crystallize" is accurate although it is believed that the hydrated polymorph is probably crystalline.

The second stage lyophilization can be carried out under the same or milder conditions than the first stage. The second stage conditions are selected such that water bound to the cyclophosphamide monohydrate and the bulking agent (some bulking agents bind water and other bulking agents do not) is not removed in the second stage. Typical second stage conditions begin with shelf temperatures of about $0°$ C. to $-30°$ C. After the solution is completely frozen, the pressure is reduced to about 500 to 8000 microns and the condensor is activated. The shelf temperature is then raised to $0°$ C. and the cake is allowed to warm gradually to that temperature. As explained earlier, these conditions will also vary somewhat with the nature of the bulking agent as well as the lyophilizer capacity, the vial size, the number of vials, etc. Once the cake reaches the shelf temperature (about 2 hours), the process is usually complete.

The lyophilizate of the present invention will contain the bound water, the cyclophosphamide and the bulking agent. The amount of water in the lyophilizate will vary with the nature of the excipient since some excipients will bind water and others will not. In the case of a cyclophosphamide-lactose product containing equal amounts of lactose and cyclophosphamide, the lyophilizate contains about 5.5% to 6.0% water (Karl-Fischer procedure).

The invention will be illustrated in more detail by the following non-limiting example.

EXAMPLE

A bulk solution was prepared containing 30 mg/ml cyclophosphamide and 30 mg/ml lactose. 10ml of the solution was placed in 100 20ml vials (nominal). The vials were placed in a lyophilization chamber. As shown in FIG. 1, the temperature was rapidly reduced to −30° C. and held at this temperature for 4 to 5 hours until the solution was completely frozen. The condenser in the chamber was activated, the chamber was evacuated to 500 microns. The vials were held at this condition 1 hour after which the shelf temperature was raised to 0° C. The vials were held for 10 hours. As seen in FIG. 2 in this time, the product temperature reached about −20° C. About 60 to 70% of the water was removed from the vial. At this time, the first stage lyophilization process was stopped, the vacuum and condenser were turned off, chamber pressure was restored to atmospheric pressure and the shelf temperature was allowed to increase to 25° C. to melt the frozen cake and precipitate the cyclophosphamide.

After 3-4 hours, precipitation was complete and the second stage lyophilization process was then initiated by rapidly freezing the samples to −30° C. The samples were held for 5 hours until the solution was frozen. The condenser was activated and the pressure was reduced to 500 microns. The vials were held for 1 hour and shelf temperature was then allowed to warm to 0° C. Two hours after the shelf temperature reached 0° C., the product temperature reached 0° C. and the process was completed. The lyophilizate contained 5.5-6% water as determined by Karl-Fischer.

Fifty of the vials were placed on stability testing at 5° C. and 37° C. for six weeks. The results are shown in Table 1 below. To demonstrate the importance of retaining the cyclophosphamide as the monohydrate, fifty additional vials were also placed in a vacuum oven to drive off the bound water and convert the monohydrate to the anhydrous form. These vials were also subjected to stability testing. The results are shown in Table 2. The results clearly show the superior stability of the lyophilizate prepared in accordance with the invention as compared to its anhydrous counterpart.

TABLE 1

| Temp. (°C.) | Time (weeks) | Conc. (mg/vial) | Avg. (mg/vial) | Percent of Initial |
|---|---|---|---|---|
| initial | | 294.4 | 294.4 | 100 |
| 5 | 6 | 299.3 | 299.3 | 102 |
| 37 | 6 | 294.9 | | |
| | | 288.4 | 291.6 | 99 |

TABLE 2

| Temp. (°C.) | Time (weeks) | Conc. (mg/vial) | Avg. (mg/vial) | Percent of Initial |
|---|---|---|---|---|
| initial | | 294.3 | 294.3 | 100 |
| 5 | 6 | 300.1 | | |
| | | 300.0 | 300.6 | 102 |
| 37 | 6 | 141.5 | | 48 |
| | | 130.4 | | 44 |
| | | 247.7 | | 84 |
| | | 109.3 | | 37 |

In summary, one manifestation of the present invention is a method for lyophilizing cyclophosphamide comprising the steps of freezing a bulk solution containing cyclophosphamide, a bulking agent, and water; removing a first portion of water from the frozen solution by lyophilization such that upon melting the solution, a solution supersaturated with cyclophosphamide is obtained; melting the solution to produce said supersaturated solution; precipitating the cyclophosphamide from the solution as a hydrated polymorph; refreezing the solution; and removing by lyophilization water not bound to the cyclophosphamide as a monohydrate or bound to the bulking agent.

In accordance with a preferred embodiment of the invention, the bulking agent is an amorphous bulking agent and, more particularly, a bulking agent selected from the group consisting of lactose, mannitol, glycine and valine. In a most preferred embodiment of the invention, the bulking agent is lactose.

Preferably, the bulk solution contains about 3 to 3.3% cyclophosphamide and about 2 to 7% bulking agent and, more particularly, lactose.

The first stage lyophilization is initiated at a temperature lower than −15° C. and, most preferably, about −30° C. After cooling, the vials are held for several hours to completely freeze them and then the pressure is reduced and the condenser is activated. Pressures up to 8000 microns can be used but the preferred pressure is about 500 microns. The second stage lyophilization conditions are similar or milder than the first stage.

Another manifestation of the invention is a pharmaceutical preparation comprising a lyophilized cake including cyclophosphamide monohydrate and lactose. The lactose is present in an amount of about 0.3 to 1.7 parts per 1 part cyclophosphamide. Preferably, the lactose and cyclophosphamide are present in equal amounts and the cake contains about 5.5 to 6% water. While not desiring to be bound, it is believed that lyophilizates containing cyclophosphamide and lactose prepared by the foregoing process have a unique crystal structure which renders them readily soluble and improves chemical and physical stability.

Having described the invention in detail and by reference to preferred embodiments thereof, it will be apparent that modifications and variations are possible without departing from the scope of the invention defined in the appended claims.

What is claimed is:

1. A pharmaceutical preparation consisting essentially of a lyophilized cake of cyclophosphamide monohydrate and lactose wherein said cake is prepared by the process of
   freezing a bulk solution containing cyclophosphamide, lactose, and water;
   removing a first portion of the water from said frozen solution by lyophilization, such that upon melting said cake a solution supersaturated with said cyclophosphamide and said lactose is obtained;
   melting said solution to produce said supersaturated solution;
   precipitating said cyclophosphamide as a hydrated polymorph;
   re-freezing said solution; and
   removing by lyophilization water not bound to said cyclophosphamide or said lactose to yield a lyophilizate consisting essentially of cyclophosphamide monohydrate and said lactose.

2. The pharmaceutical preparation of claim 1 wherein, said bulk solution contains said cyclophosphamide in an amount of about 3.0 to 3.3 percent and said lactose in an amount of about 2 to 7 percent.

3. The pharmaceutical preparation of claim 1 wherein said lactose is present in an amount of about 0.3 to 1.7 parts per 1 part said cyclophosphamide monohydrate.

4. The pharmaceutical preparation of claim 3 wherein said lactose and said cyclophosphamide monohydrate are present in approximately equal amounts.

* * * * *